(12) United States Patent
Wang et al.

(10) Patent No.: US 8,075,524 B2
(45) Date of Patent: Dec. 13, 2011

(54) SYRINGE SET AND HEATING DEVICE FOR SAME

(75) Inventors: Jia-Ping Wang, Beijing (CN); Chen Feng, Beijing (CN); Kai-Li Jiang, Beijing (CN); Liang Liu, Beijing (CN); Shou-Shan Fan, Beijing (CN)

(73) Assignees: Tsinghua University, Beijing (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 0 days.

(21) Appl. No.: 12/775,638

(22) Filed: May 7, 2010

(65) Prior Publication Data
US 2010/0305504 A1 Dec. 2, 2010

(30) Foreign Application Priority Data
Jun. 2, 2009 (CN) .......................... 2009 1 0107826

(51) Int. Cl.
*A61F 7/12* (2006.01)
(52) U.S. Cl. ......................................... 604/114; 607/98
(58) Field of Classification Search ............... 604/93.01, 604/113–114
See application file for complete search history.

(56) References Cited

U.S. PATENT DOCUMENTS

| | | | |
|---|---|---|---|
| 6,179,805 B1 * | 1/2001 | Sussman et al. | 604/27 |
| 7,045,108 B2 | 5/2006 | Jiang et al. | |
| 2005/0261670 A1 * | 11/2005 | Weber et al. | 606/21 |
| 2007/0166223 A1 | 7/2007 | Jiang et al. | |
| 2008/0170982 A1 | 7/2008 | Zhang et al. | |
| 2008/0248235 A1 | 10/2008 | Feng et al. | |

FOREIGN PATENT DOCUMENTS
CN 2327393 7/1999
* cited by examiner

*Primary Examiner* — Nicholas Lucchesi
*Assistant Examiner* — Melissa A Snyder
(74) *Attorney, Agent, or Firm* — Altis Law Group, Inc.

(57) ABSTRACT

A syringe set includes a syringe and a heating device. The heating device includes a heating module in thermal engagement with the syringe and a body supporting the heating module. The heating module includes a first electrode, a second electrode and a heating element. The heating element includes a plurality of carbon nanotubes forming at least one electrically conductive path. The first electrode and the second electrode electrically connect with the carbon nanotubes.

20 Claims, 14 Drawing Sheets

SYRINGE SET AND HEATING DEVICE FOR SAME

RELATED APPLICATIONS

This application claims all benefits accruing under 35 U.S.C. §119 from China Patent Application No. 200910107826.7, filed on Jun. 2, 2009 in the China Intellectual Property Office, the disclosure of which is incorporated herein by reference.

BACKGROUND

1. Technical Field

The present disclosure relates to syringe sets or injectors and heating devices for the same. Specifically, the present disclosure relates to a syringe set incorporating carbon nanotubes as a heating device.

2. Description of Related Art

During many medical procedures, various pharmaceuticals and medical fluids are injected into living organisms for purposes of diagnosis or treatment via syringes or injectors. Conventionally, a syringe and medical fluid therein may be warmed to a temperature near body temperature before the medical fluid is injected into a patient's circulatory system. Heating the medical fluid provides a benefit of reducing patient discomfort by reducing temperature mismatch. An additional benefit of heating the medical fluid is reduction in viscosity, which permits the medical fluid to be injected with less effort or at a higher rate.

Conventionally, the syringe carrying the medical fluid is held at approximately body temperature in a heated enclosure, such as a warmer box, and is transferred away from the warmer box shortly before the medical procedure is scheduled to commence. After being removed from the warmer box, the syringe and medical fluid immediately begin to cool toward room temperature. The extent of the cooling depends upon the time delay before the injection commences and the duration of the injection. In some instances, the medical fluid is not injected for several minutes after the syringe is removed from the warmer box. This permits the temperature of the medical fluid to drop significantly before being delivered to a patient's circulatory system.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments.

DETAILED DESCRIPTION OF EXEMPLARY EMBODIMENTS

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
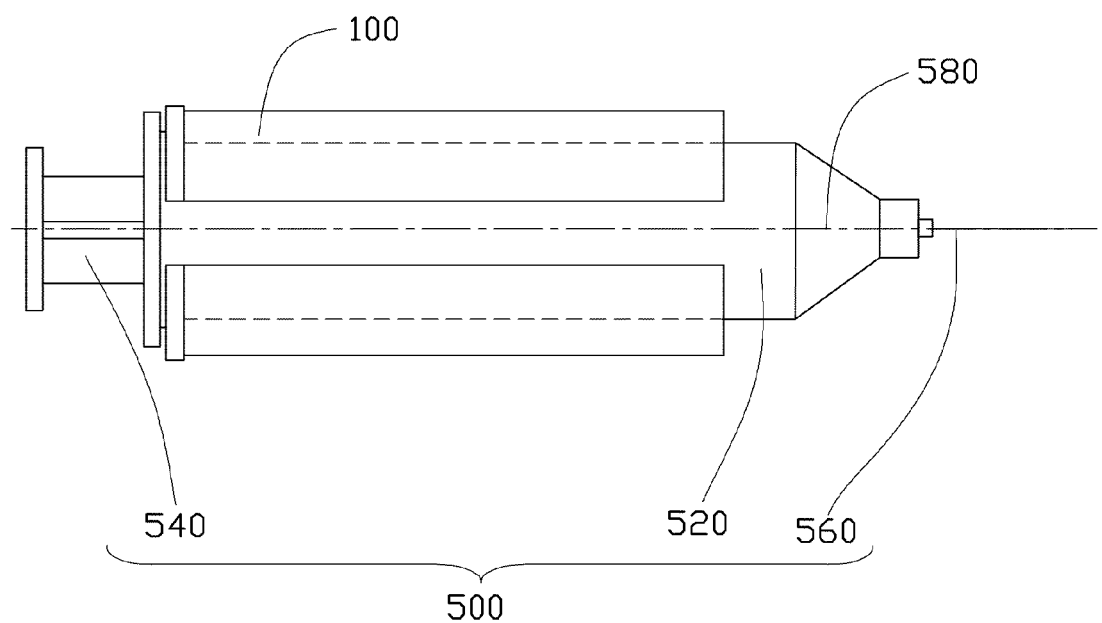
FIG. 1 is a schematic structural view of one embodiment of a syringe set.

One embodiment of a syringe set is illustrated in FIG. 1. The syringe set comprises a syringe 500 and a heating device 100 used to heat the syringe 500 with fluid contained therein.

Figure 2:
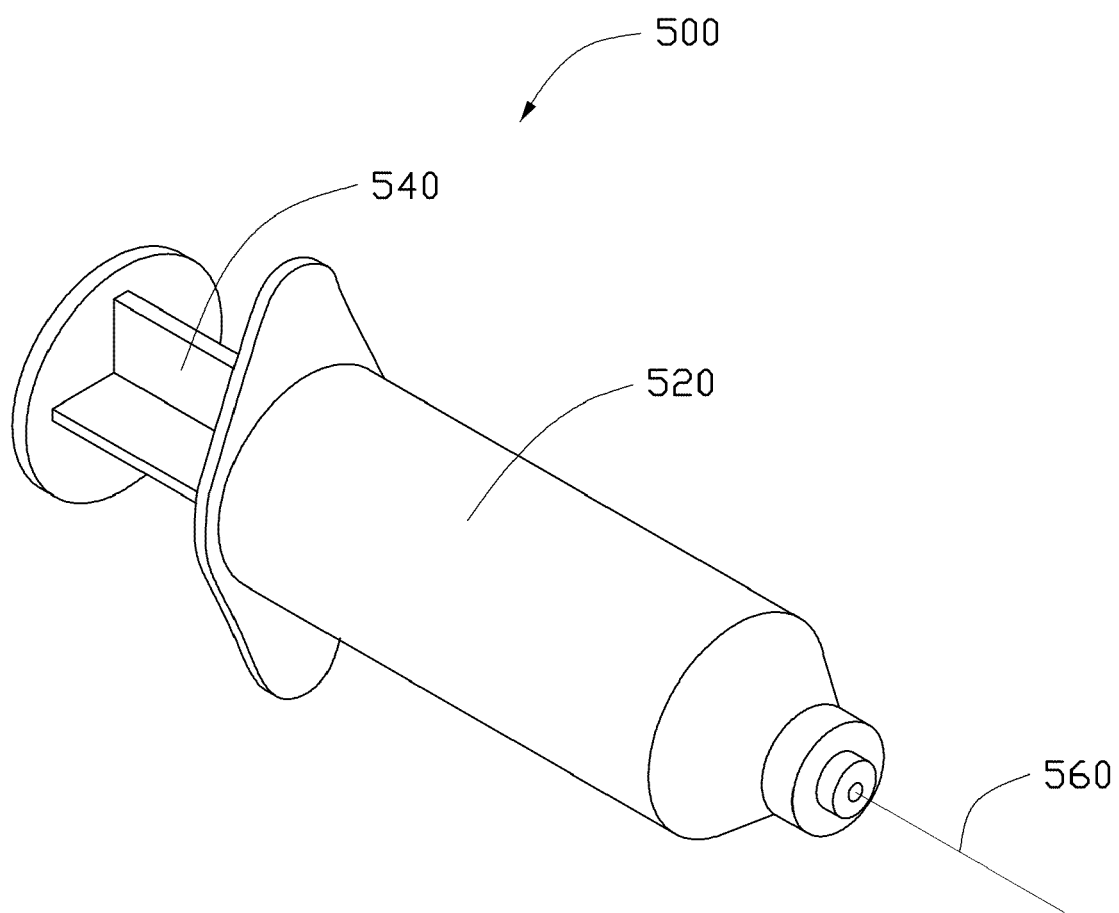
FIG. 2 is an enlarged view of a syringe of the syringe set of FIG. 1.

An enlarged view of the syringe 500 is shown in FIG. 2. The syringe 500 comprises a tubular sidewall 520, a syringe plunger 540 received in the tubular sidewall 520 and a needle 560. The tubular sidewall 520 can be in the form of a hollow cylindrical barrel. The syringe plunger 540 can be slidably installed in the interior of the tubular sidewall 520 from a left end of the tubular sidewall 520. The syringe plunger 540 is contoured to at least generally conform to the shape of the interior of the tubular sidewall 520. The syringe plunger 540 can be driven to move relative to the tubular sidewall 520 so that fluid contained in the tubular sidewall 520 can be expelled out into a patient's circulatory system through the needle 560. The needle 560 is installed on a right end of the tubular sidewall 520.

It is noteworthy that the syringe 500 can also be a drip syringe (not shown) which usually comprises a transfusion bottle, an infusion tube and a needle fluidly connected to the transfusion bottle through the infusion tube. Other medical containers which are needed to be heated can also be heated by the heating device 100 in similar manner.

Figure 3:
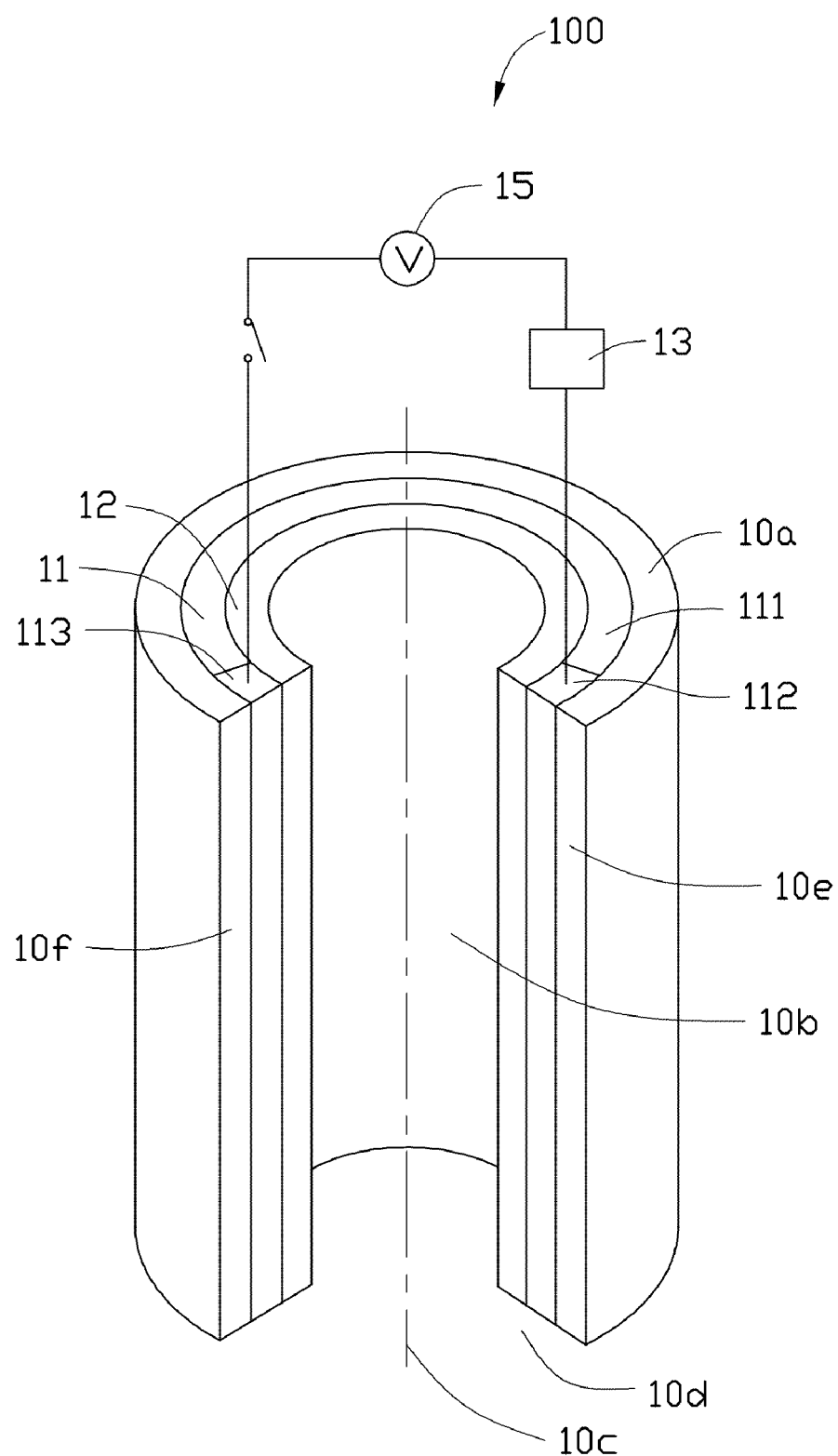
FIG. 3 is an enlarged view of a heating device of the syringe set of FIG. 1.
Figure 4:
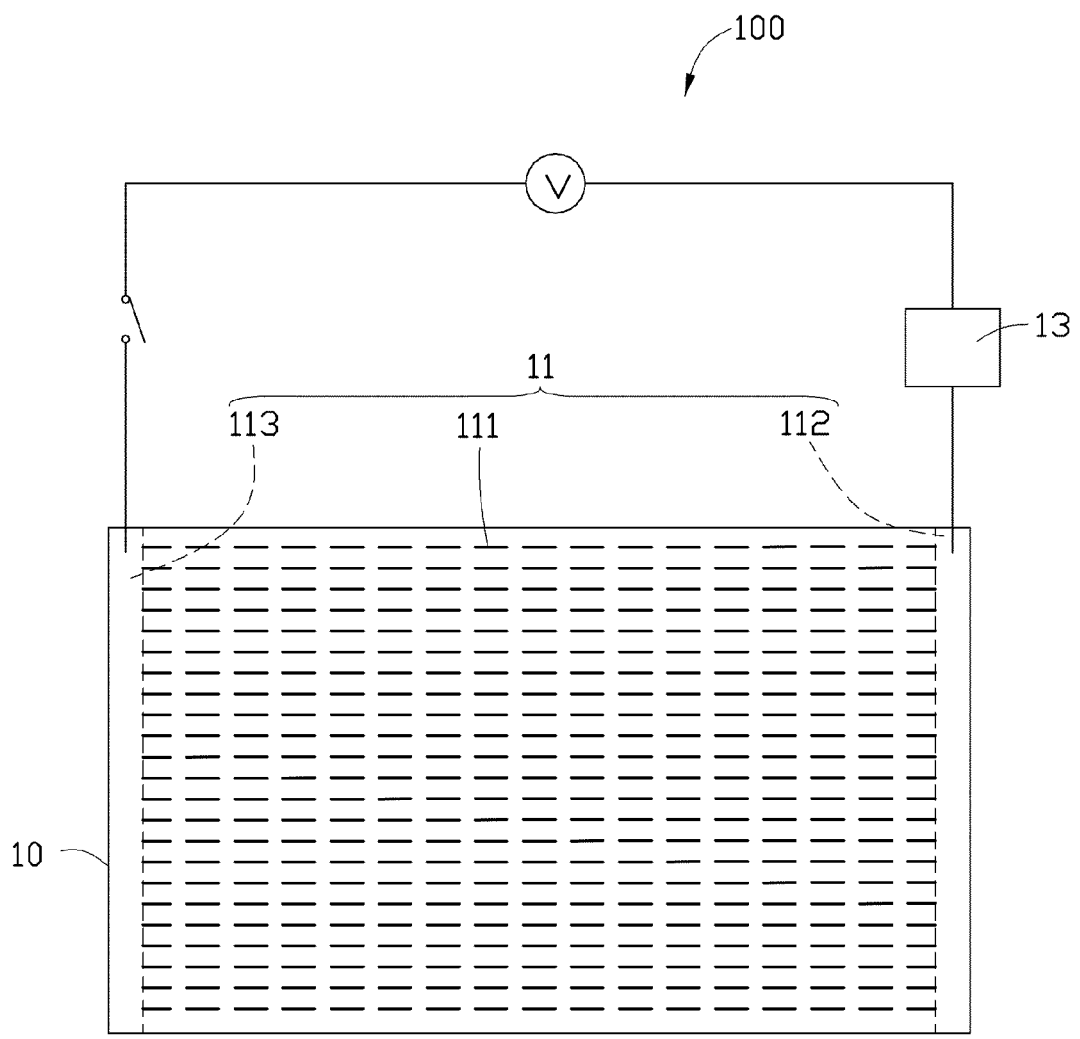
FIG. 4 is a flat layout of the heating device of FIG. 3.
Figure 5:
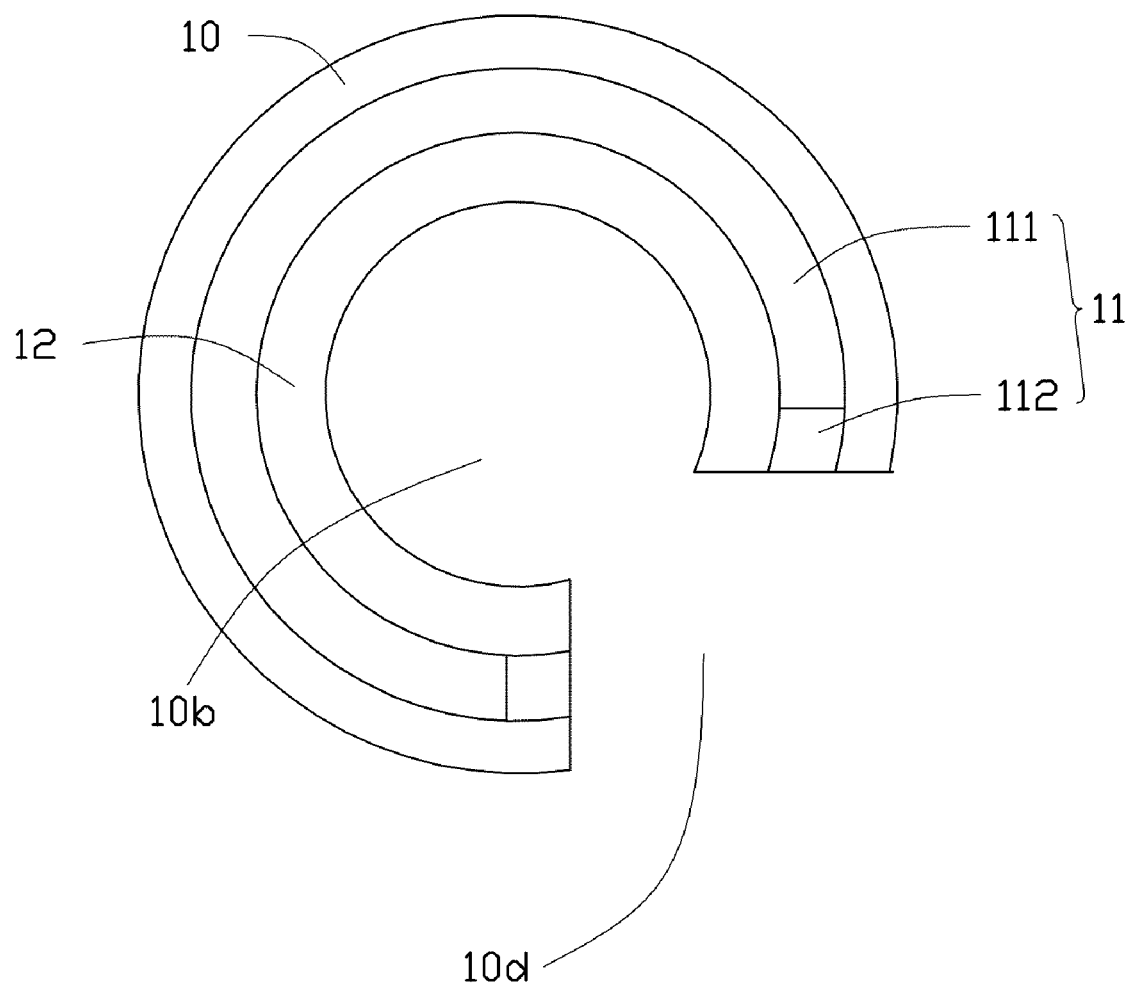
FIG. 5 is a top plan view of the heating device of FIG. 3.

Referring to FIGS. 3-5, the heating device 100 comprises a jacket or body 10, a heating module 11, and can also comprise a protective structure 12. The heating module 11 is installed between the body 10 and the protective structure 12. The protective structure 12 can be used to protect the heating module 11.

The body 10 can be made of insulated thermally conductive materials. For example, if the body 10 is rigid it can be made of ceramic, acrylic, polypropylene, polycarbonate, polyethylene, thermosetting resin, or wood. The thermosetting resin can be phenolic resin, epoxide resin, amino resin, or unsaturated polyester resin.

As shown in FIG. 3, the body 10 is made of polycarbonate and is rigid, the body 10 has a substantially tubular jacket sidewall 10a shaped and sized to receive a portion of the tubular sidewall 520. The jacket sidewall 10a extends along and is centered about a longitudinal axis 10c of the heating device 100. As shown in FIG. 5, the top plan view of the body 10 is generally C-shaped with a slot 10d. The slot 10d extends along the axial length of the body 10, and separates a pair of edges 10e and 10f. The slot 10d permits an observer to perceive the position of the syringe plunger 540 and its head, during a procedure. The slot 10d also provides access to the cavity 10*b*, which permits the tubular sidewall 520 to remain coupled with the needle 560 during loading and unloading. Alternatively, the slot 10*d* may be omitted.

Alternatively, the body 10 can be made of flexible materials, such as cloth, silicon rubber, silk, leather, paper, or flexible plastic. The flexible plastic can be polyurethane resin, flexible rubber, styrene, glycerol, phthalic anhydride, or maleic anhydride. If the body 10 is flexible, the body 10 can be easily attached to an outer surface of the tubular sidewall 520 or other medical containers needed to be heated, and can be secured thereon elastically, by adhesive tape or other methods.

Figure 6:
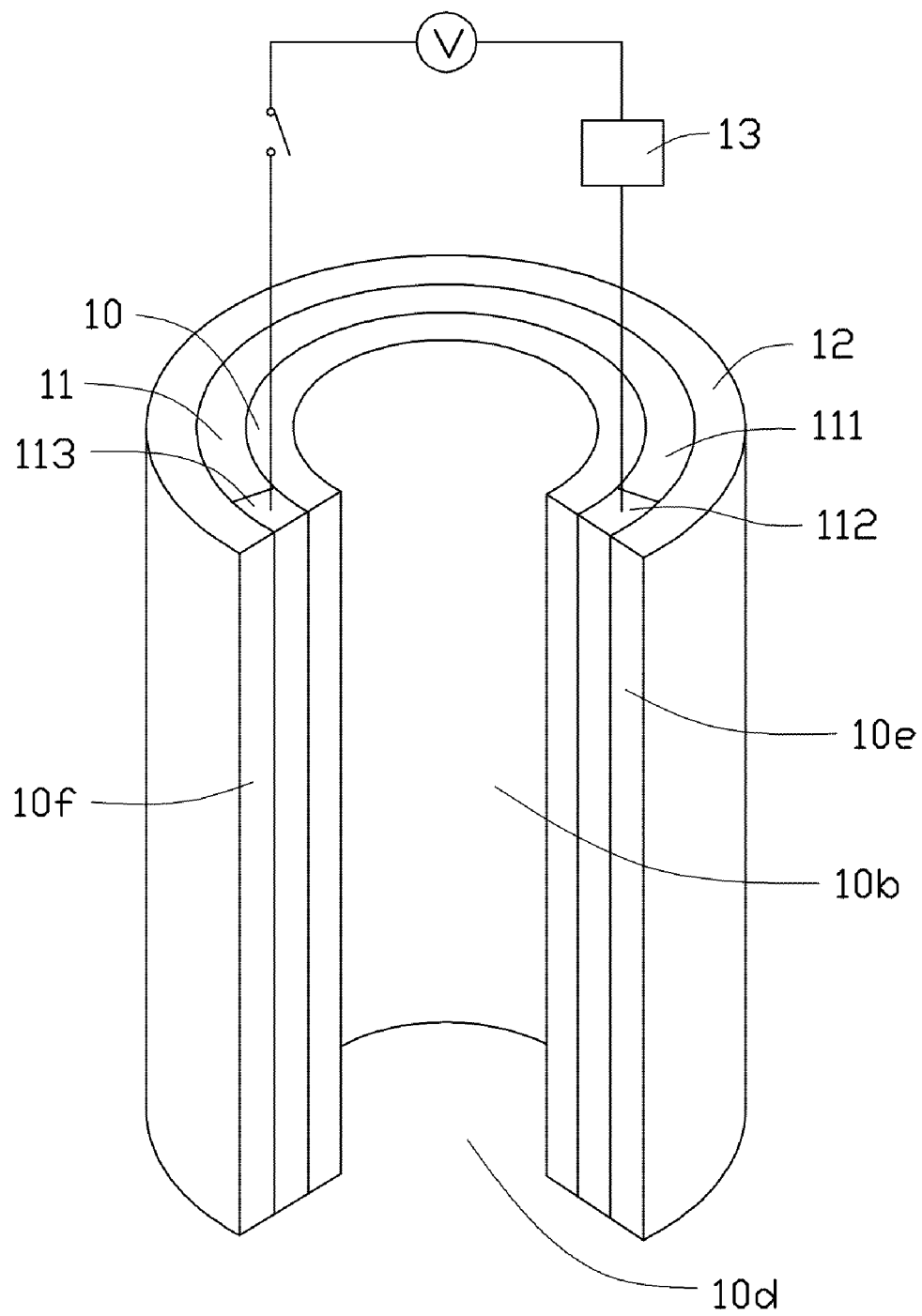
FIG. 6 is a schematic structural view of another embodiment of a heating device of a syringe set.
Figure 7:
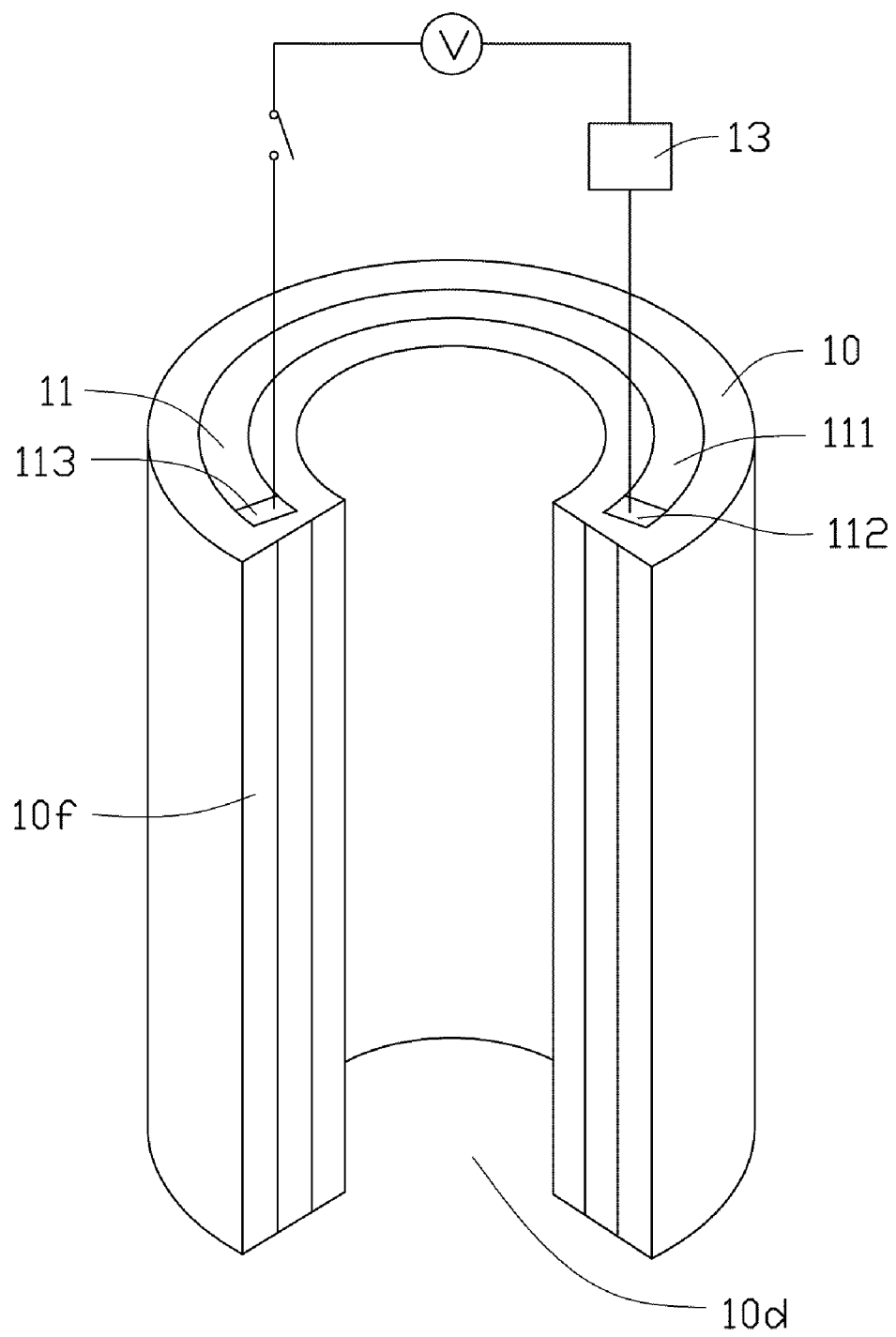
FIG. 7 is a schematic structural view of yet another embodiment of a heating device of a syringe set.

The heating module 11 comprises a heating element 111, a first electrode 112 and a second electrode 113. The first electrode 112 and the second electrode 113 are electrically connected to the heating element 111 and are spaced from each other. The heating element 11 can be disposed on the inner surface of the body 10 as shown in FIG. 3, or on the outer surface of the body 10 as shown in FIG. 6, or embedded in the body 10 without the protective structure 12 as shown in FIG. 7.

If the heating element 11 is disposed on the inner surface of the body 10 as shown in FIG. 3, the protective structure 12 is made of materials having good thermal conductivity. If the heating element 11 is disposed on the outer surface of the body 10 as shown in FIG. 6, the body 10 is made of materials having good thermal conductivity. If the heating element 11 is embedded in the body 10 without the protective structure 12 as shown in FIG. 7, the body 10 is made of insulated materials having good thermal conductivity.

The heating element 111 comprises a plurality of carbon nanotubes. The carbon nanotubes can be selected from single-walled, double-walled, and/or multi-walled carbon nanotubes. The carbon nanotubes can form into a freestanding structure. The term "freestanding" includes, but is not limited to, a structure that does not have to be supported by a substrate and can sustain its own weight when hoisted by a portion thereof without any significant damage to its structural integrity. The carbon nanotubes can be arranged to form a layer-shaped carbon nanotube structure or a linear carbon nanotube structure. If the carbon nanotubes form a layer-shaped carbon nanotube structure, the layer-shaped carbon nanotube structure can be directly spread on the body 10, as shown in FIG. 3 and FIG. 6. If the carbon nanotubes form a linear carbon nanotube structure, the linear carbon nanotube structure can be arranged on the body 10 to form a zigzag or a rectangular ambulatory.

When the carbon nanotubes form a layer-shaped carbon nanotube structure, the layer-shaped carbon nanotube structure has a thickness ranging from about 0.5 nanometers (nm) to about 1 mm. In one embodiment, the layer-shaped carbon nanotube structure has a thickness of about 50 nanometers. The layer-shaped carbon nanotube structure can comprise at least one carbon nanotube film. In detail, the layer-shaped carbon nanotube structure can comprise two or more carbon nanotube films stacked, coplanar or both stacked and coplanar with each other. The carbon nanotube film comprises a plurality of uniformly distributed carbon nanotubes connected by Van der Waals attractive force.

The carbon nanotubes in the carbon nanotube film can be arranged orderly. The carbon nanotube film including ordered carbon nanotubes is an ordered carbon nanotube film. The term 'ordered carbon nanotube film' refers to a film where the carbon nanotubes are arranged in a consistently systematic manner, e.g., the carbon nanotubes are arranged approximately along a same direction and/or have two or more sections within each of which the carbon nanotubes are arranged approximately along a same direction (different sections can have different directions).

In one embodiment, the carbon nanotube film structure includes at least one drawn carbon nanotube film. A film can be drawn from a carbon nanotube array, to obtain a drawn carbon nanotube film. Examples of drawn carbon nanotube film are taught by U.S. Pat. No. 7,045,108 to Jiang et al., and US Patent Application Pub. No. US 2008/0170982 to Zhang et al. The drawn carbon nanotube film includes a plurality of successive and oriented carbon nanotubes joined end-to-end by van der Waals attractive force therebetween. The drawn carbon nanotube film is a free-standing film.

Figure 8:
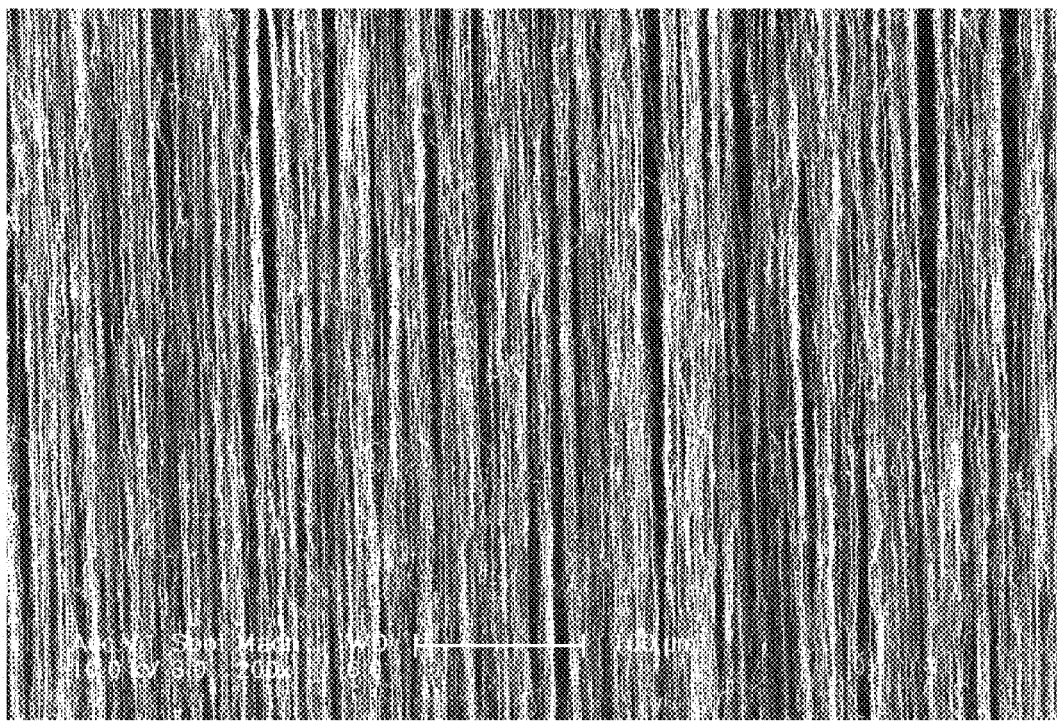
FIG. 8 shows a Scanning Electron Microscope (SEM) image of one embodiment of an ordered carbon nanotube film.
Figure 9:
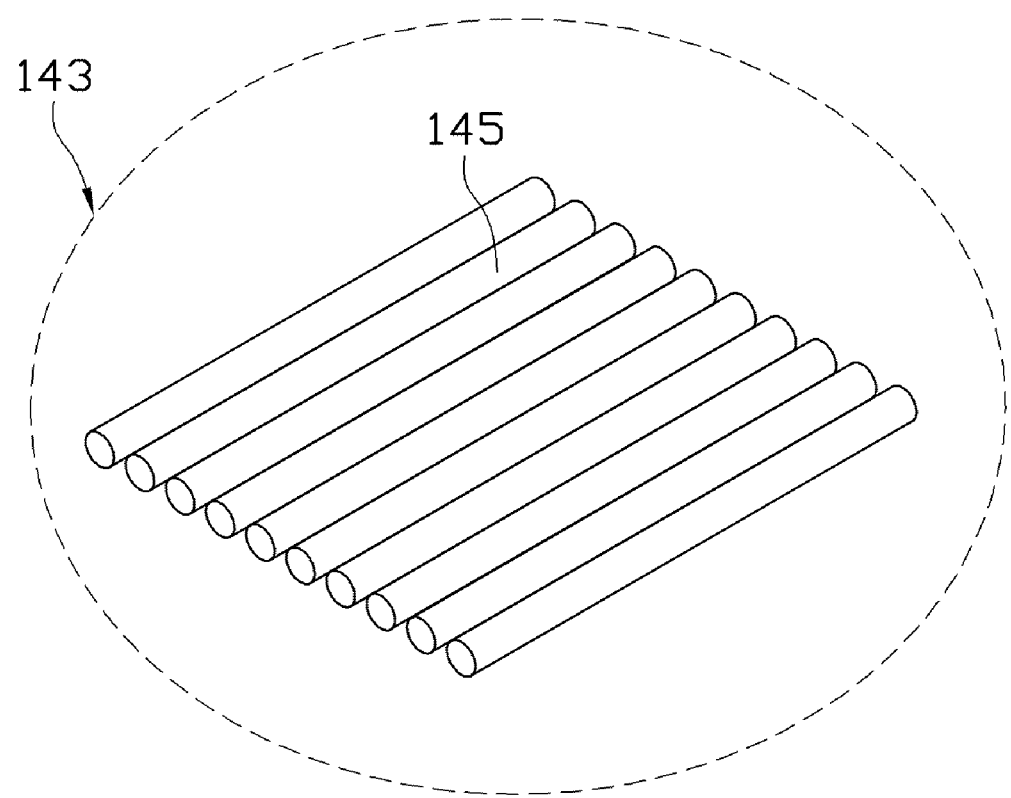
FIG. 9 is a schematic, enlarged view of a carbon nanotube segment in the ordered carbon nanotube film of FIG. 8.

FIG. 8 and FIG. 9 show a drawn carbon nanotube film. The drawn carbon nanotube film includes a plurality of successively oriented carbon nanotube segments 143 joined end-to-end by van der Waals attractive force therebetween. Each carbon nanotube segment 143 includes a plurality of carbon nanotubes 145 substantially parallel to each other, and combined by van der Waals attractive force therebetween.

As can be seen in FIG. 8, some variations can occur in the drawn carbon nanotube film. The carbon nanotubes 145 in the drawn carbon nanotube film are substantially oriented along a preferred orientation. The carbon nanotube film can be treated with an organic solvent to increase the mechanical strength and toughness of the carbon nanotube film and reduce the coefficient of friction of the carbon nanotube film. The thickness of the carbon nanotube film can range from about 0.5 nm to about 100 µm. When the carbon nanotube film shown in FIG. 8 is used as a layer-shaped carbon nanotube structure, the carbon nanotubes 145 in the drawn carbon nanotube film are substantially oriented along a preferred orientation from the first electrode 112 to the second electrode 113.

In other embodiment, the layer-shaped carbon nanotube structure can include two or more coplanar carbon nanotube films, and can include layers of coplanar carbon nanotube films. Additionally, when the carbon nanotubes in the carbon nanotube film are aligned along one preferred orientation (e.g., the drawn carbon nanotube film), an angle can exist between the orientations of carbon nanotubes in adjacent films, whether stacked or adjacent. Adjacent carbon nanotube films can be combined by only the van der Waals attractive force therebetween. An angle between the aligned directions of the carbon nanotubes in two adjacent carbon nanotube films can range from about 0 degrees to about 90 degrees. Stacking the carbon nanotube films will add to the structural integrity of the layer-shaped carbon nanotube structure.

Figure 10:
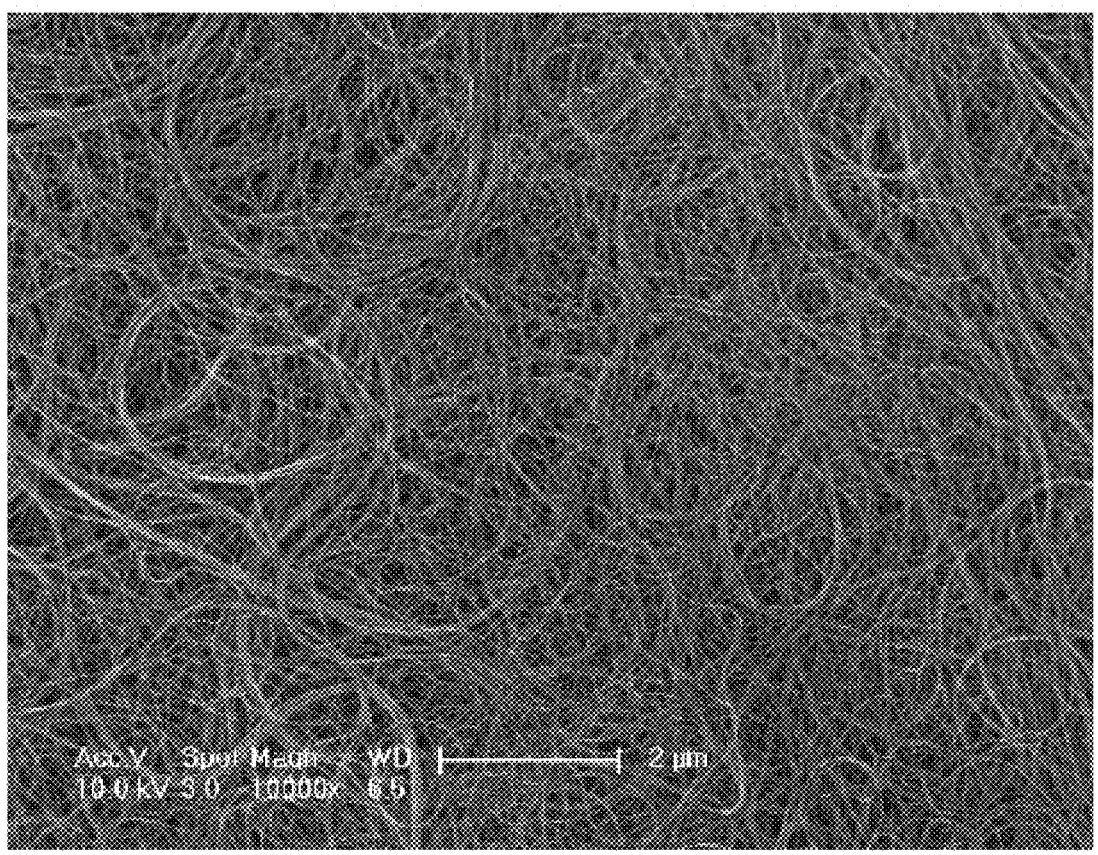
FIG. 10 shows an SEM image of one embodiment of a disordered carbon nanotube film.

FIG. 10 shows an SEM image of one embodiment of a disordered carbon nanotube film. A carbon nanotube film including disordered carbon nanotubes is a disordered carbon nanotube film. The term 'disordered carbon nanotube film' refers to a structure where the carbon nanotubes are arranged along different directions, and the aligning directions of the carbon nanotubes are random. The number of the carbon nanotubes arranged along each different direction can be almost the same (e.g. uniformly disordered). The disordered carbon nanotube film can be isotropic, namely the disordered carbon nanotube film has properties identical in all directions of the disordered carbon nanotube film. The carbon nanotubes in the disordered carbon nanotube structure can be entangled with each other.

The disordered carbon nanotube film shown in FIG. 10 is a flocculated carbon nanotube film. The thickness of the flocculated carbon nanotube film can range from about 1 nm to about 1 mm. The flocculated carbon nanotube film can include a plurality of long, curved, disordered carbon nanotubes entangled with each other. Further, the flocculated carbon nanotube film can be isotropic. The carbon nanotubes can be substantially uniformly dispersed in the flocculated carbon nanotube film. Adjacent carbon nanotubes are acted upon by van der Waals attractive force to obtain an entangled structure with micropores defined therein. Sizes of the micropores can be less than 10 μm. The porous nature of the flocculated carbon nanotube film will increase specific surface area of the carbon nanotube structure.

Further, due to the carbon nanotubes in the carbon nanotube film being entangled with each other, the carbon nanotube structure employing the flocculated carbon nanotube film has excellent durability, and can be fashioned into desired shapes with a low risk to the integrity of the carbon nanotube structure.

In one embodiment, the linear carbon nanotube structure can include one or more carbon nanotube wires. The carbon nanotube wires can be substantially parallel to each other to form a bundle-like structure or twisted with each other to form a twisted structure.

Figure 11:
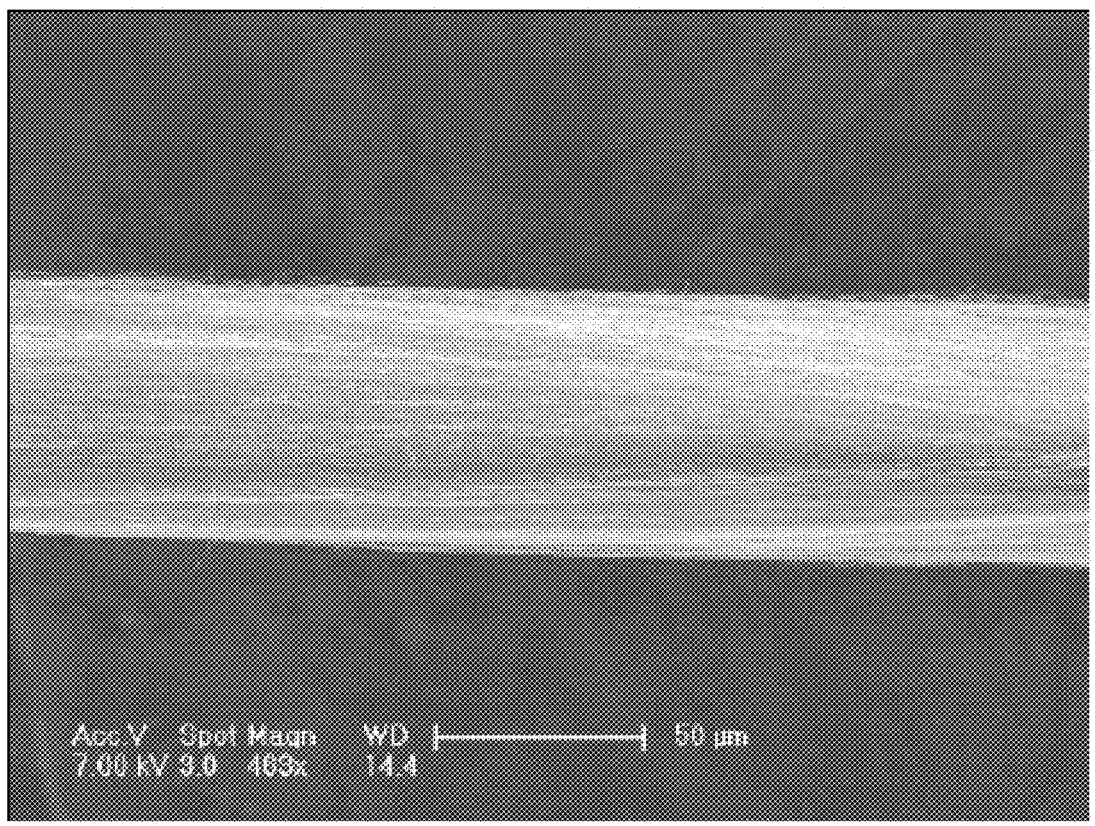
FIG. 11 shows an SEM image of one embodiment of an untwisted carbon nanotube wire.

The carbon nanotube wire can be an untwisted carbon nanotube wire or a twisted carbon nanotube wire. An untwisted carbon nanotube wire is formed by treating a carbon nanotube film with an organic solvent. FIG. 11 shows an untwisted carbon nanotube wire and the untwisted carbon nanotube wire includes a plurality of successive carbon nanotubes, which are substantially oriented along the linear direction of the untwisted carbon nanotube wire and joined end-to-end by van der Waals attraction force therebetween. The untwisted carbon nanotube wire has a diameter ranging from about 0.5 nm to about 100 μm.

Figure 12:
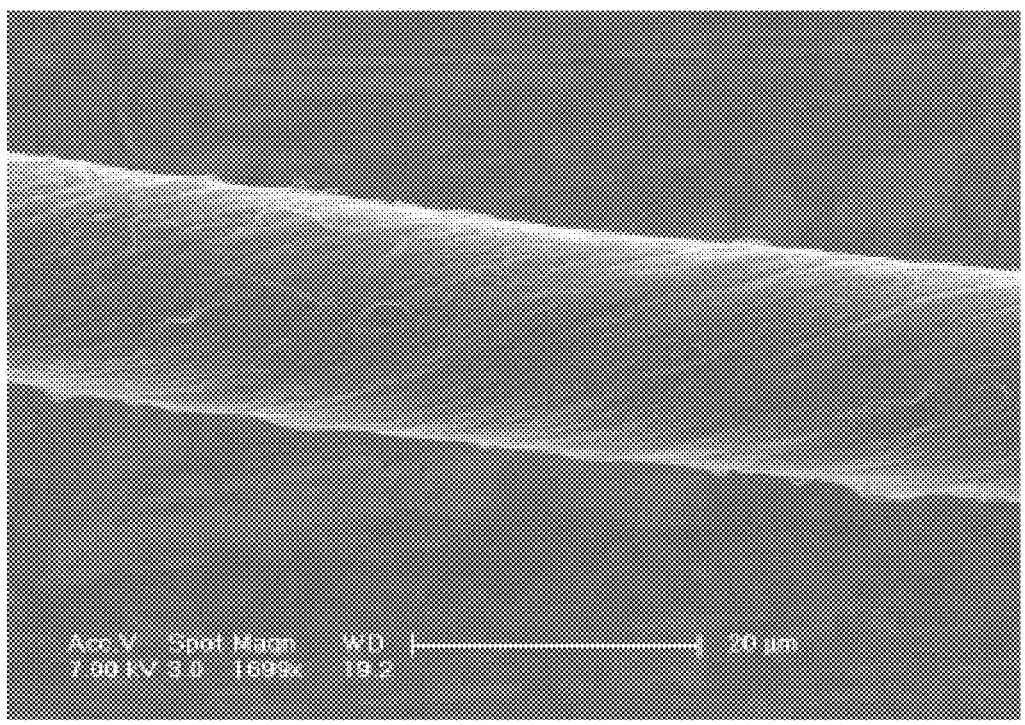
FIG. 12 shows an SEM image of one embodiment of a twisted carbon nanotube wire.

A twisted carbon nanotube wire is formed by twisting a carbon nanotube film by using a mechanical force. FIG. 12 shows a twisted carbon nanotube wire and the twisted carbon nanotube wire includes a plurality of carbon nanotubes oriented around an axial direction of the twisted carbon nanotube wire. The length of the twisted carbon nanotube wire can be set as desired and the diameter of the carbon nanotube wire can range from about 0.5 nanometers to about 100 micrometers. The twisted carbon nanotube wire can be treated with an organic solvent before or after twisting. An example of the untwisted carbon nanotube wire and a method for manufacturing the same has been taught by US Patent Application Pub. No. US 2007/0166223, the disclosure of which is incorporated herein by reference.

It is noteworthy that the heating module 11 may include a plurality of twisted carbon nanotube wires or untwisted carbon nanotube wires, which can be crossed with each other or weaved together.

In the embodiment shown in FIG. 3 and FIG. 4, the heating element 111 is a layer-shaped carbon nanotube structure, which comprises a plurality of carbon nanotube films stacked one upon another. The carbon nanotubes in the layer-shaped carbon nanotube structure are substantially oriented along a preferred orientation, which is from the first electrode 112 to the second electrode 113. The layer-shaped carbon nanotube structure has a thickness of about 100 μm. A flat layout of the layer-shaped carbon nanotube structure is square and has four equal sides of about 18 centimeters.

The heating module 11 will not be damaged after being bent many times due to the good flexibility of the carbon nanotube film and the carbon nanotube wire. If the body 10 and the protective structure 12 are also made of flexible materials, the heating device 100 is then flexible. Thus, the heating device 100 can be bent into a desired shape according to varied outer surfaces of the tubular sidewall 520 or a container needed to be heated.

Furthermore, if the layer-shaped carbon nanotube structure has a small thickness, for example, smaller than 10 μm, the layer-shaped carbon nanotube structure has good transparency and the light transmittance is about 95%. If the carbon nanotube wire has a small diameter, for example, smaller than 10 μm, the carbon nanotube wire has good transparency and the light transmittance is about 95%. Then, the heating device 100 is transparent when the first electrode 112, the second electrode 113 and the body 10 are also made of transparent materials. For example, the first electrode 112 and the second electrode 113 can be made of transparent materials, such as indium tin oxide, layer-shaped carbon nanotube structure or linear carbon nanotube structure. The body 10 can be made of transparent materials, such as acrylic, polypropylene, polyethylene, polycarbonate and polyurethane.

The first electrode 112 and the second electrode 113 are made of electrically conductive materials. The shape of the first electrode 112 and the second electrode 113 is not limited. Each of the first electrode 112 and the second electrode 113 can be an electrically conductive film, sheet metal or metal down-lead. In order to reduce the total thickness of the heating device 100, the first electrode 112 and the second electrode 113 can be an electrically conductive film, which can be made of metal, alloy, ITO, antimony tin oxide (ATO), conductive silver glue, electro-conductive polymer, or electrical conductive carbon nanotubes. The metal or alloy can be aluminum, copper, tungsten, molybdenum, gold, titanium, neodymium, palladium, or combination thereof.

In the embodiment shown in FIG. 3 and FIG. 4, there is one first electrode 112 and one second electrode 113, and each of the first electrode 112 and the second electrode 113 is a film of palladium. The film of palladium has a thickness of about 1 μm. Palladium and carbon nanotubes have good wettability and contribute to form good electrical contact between the first electrode 112 and the heating module 111, and between the second electrode 113 and the heating module 113.

The first electrode 112 and the second electrode 113 can be disposed on the surface of the body 10 by sputtering deposition, electrochemical process, direct writing method, or silkscreen print method. In the embodiment shown in FIGS. 3-4, the first electrode 112 and the second electrode 113, are spaced, and disposed on the heating element 111 in the form of a strip by silkscreen print method. The strip-shaped first electrode 112 and the second electrode 113 extend along the longitudinal axis 10c of the heating device 100. The carbon nanotubes of the heating element 111 are oriented along the direction from the first electrode 112 to the second electrode 113, and substantially perpendicular to the first electrode 112 and the second electrode 113 as shown in FIG. 4.

The protective structure 12 is mainly used to protect the heating module 11 from being damaged and to protect a user from getting an electric shock by touching the heating module 11. The protective structure 12 can be made of electrically conductive materials with good thermal conductivity, such as metal. The metal can be stainless steel, carbon steel, copper, nickel, titanium, zinc, or aluminum. If the protective structure 12 is electrically conductive, the protective structure 12 is insulated from the heating module 11 by insulating materials or space. Alternatively, the protective structure 12 can be made of insulating materials with good thermal conductivity, such as glass. When the protective structure 12 is insulated, the protective structure 12 can contact with or space from the heating module 11.

In the embodiment shown in FIG. 3, the protective structure 12 is a transparent layer made of acrylic. The protective structure 12 is secured on the surface of the body 10 via adhesive. The protective structure 12 can also be secured on the surface of the body 10 via screws or rivets in other embodiments. It is noteworthy that the protective structure 12 can be omitted when the heating module 11 is embedded in the body 10 as shown in FIG. 7.

The heating device 100 further comprises a temperature controller 13. One end of the temperature controller 13 is connected with the first electrode 112 of the heating module 11 while the other end of the temperature controller 13 is connected with a power supply 15. The temperature controller 13 can control the temperature of the heating module 11 by adjusting the electrical current flowing through the heating element 111.

As described above, the heating device 100 can be directly and easily fixed on the tubular sidewall 520 as shown in FIG. 1 or other containers needed to be heated, thereby heating the medical fluid contained therein. The heat generated by the carbon nanotubes of the heating element 111 is invariable when the electrical current applied to the heating element 111 is invariable because the resistance of the heating module 11 is constant. This makes it easy to keep the syringe 500 at a desired temperature. Further, the carbon nanotube film or the carbon nanotube wire of the heating element 111 has good flexibility, and will not be damaged after being bent many times. This can improve the reliability of the heating device 100, and the reliability is particularly important because the heating device 100 is used to heat medical fluid during diagnosis or medical treatment.

Figure 13:
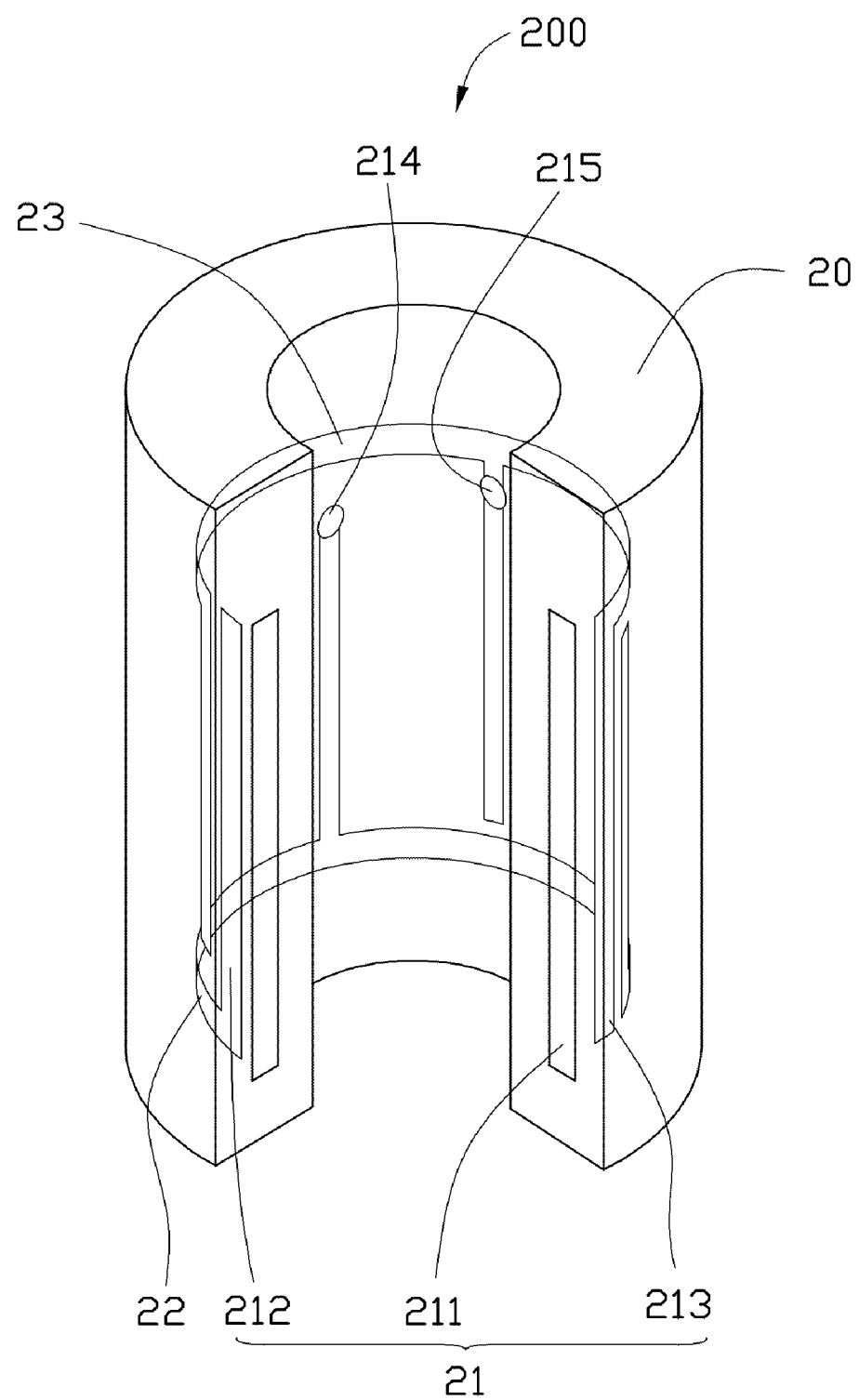
FIG. 13 is a schematic structural view of yet another embodiment of a heating device of a syringe set.
Figure 14:
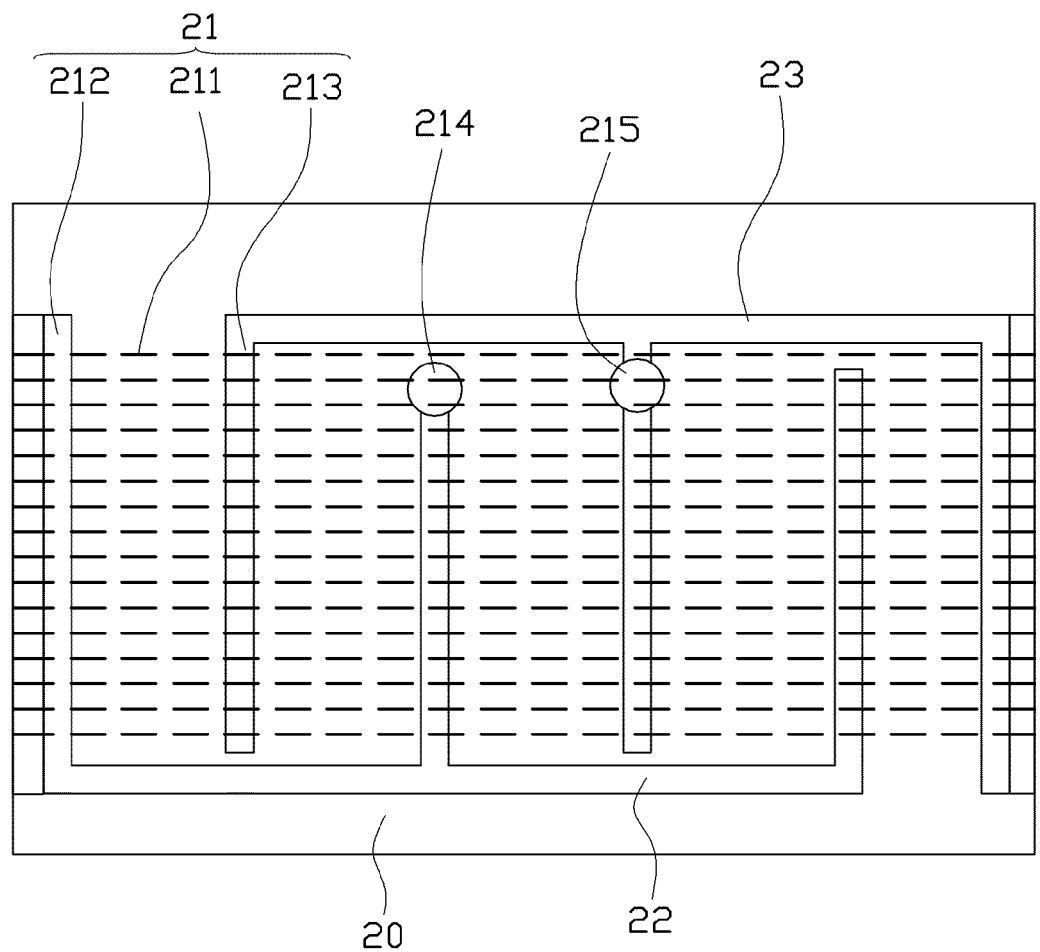
FIG. 14 is a flat layout of the heating device of FIG. 13.

Referring to the embodiment shown in FIGS. 13-14, a heating device 200 comprises a body 20 and a heating module 21 embedded in the body 20. The body 20 can be made of the same materials as that of the body 10. In the embodiment shown in FIG. 13, the body 20 is made of transparent materials. The transparent body 20 is convenient for observing the medical fluid in the syringe 500.

The heating module 21 comprises a heating element 211, a plurality of first electrodes 212 and a plurality of second electrode 213. The heating element 211 is the same as the heating element 111, and is electrically connected with the first electrodes 212 and the second electrodes 213.

As shown in FIG. 14, the first electrodes 212 and the second electrodes 213 are alternatively arranged on the heating element 211 with an interval defined between adjacent ones. The first electrodes 212 are electrically connected by a first conductive line 22. The first conductive line 22 is electrically connected to a common end of the first electrodes 212. The second electrodes 213 are electrically connected by a second conductive line 23. The second conductive line 23 is electrically connected to a common end of the second electrodes 213. The first conductive line 22 and the second conductive line 23 can be located at opposite sides of the heating element 211 and spaced apart from the heating element 211.

The first electrodes 212 and the second electrodes 213 are alternatively and parallelly arranged, resulting in a parallel connection of portions of the heating element 211 between the first electrodes 212 and the second electrodes 213. The parallel connections in the heating element 211 provide lower resistance, thus input voltage required for the heating element 211, can be lowered. The heating device 200 can work under a safe voltage, for example, of about 36 volts.

When the heating module 21 is embedded in the body 20, two lead terminals or wires are provided to electrically connect the heating module 21 to a power supply (not shown). As shown in FIG. 13 and FIG. 14, a first lead terminal or wire 214 contacts one of the first electrodes 212 and is exposed out of the body 20, and a second lead terminal or wire 215 contacts one of the second electrodes 213 and is exposed out of the body 20. The power supply can also be integrated with the heating device 100.

Finally, it is to be understood that the above-described embodiments are intended to illustrate rather than limit the present disclosure. Variations may be made to the embodiments without departing from the spirit of the disclosure as claimed. Elements associated with any of the above embodiments are envisioned to be associated with any other embodiments. The above-described embodiments illustrate the scope of the disclosure but do not restrict the scope of the disclosure.

What is claimed is:

1. A syringe set comprising:
   a syringe; and
   a heating device comprising:
      a heating module in thermal engagement with the syringe, the heating module comprising a heating element, a first electrode and a second electrode, wherein the heating element comprises a plurality of carbon nanotubes forming at least one electrically conductive path between the first electrode and the second electrode, and the first electrode and the second electrode electrically connect with the carbon nanotubes; and
      a body supporting the heating module;
      wherein the at least one electrically conductive path is adapted to convert a current into a heat and transfer the heat.

2. The syringe set of claim 1, wherein the carbon nanotubes of the heating element form a layer-shaped carbon nanotube structure or a linear carbon nanotube structure.

3. The syringe set of claim 2, wherein in the layer-shaped carbon nanotube structure, the carbon nanotubes form at least one carbon nanotube film, and the carbon nanotubes of each of the at least one carbon nanotube film are joined end-to-end by van der Waals attractive force therebetween, and the carbon nanotubes of each of the at least one carbon nanotube film are substantially aligned along a direction from the first electrode to the second electrode.

4. The syringe set of claim 2, wherein in the linear carbon nanotube structure, the carbon nanotubes form one untwisted carbon nanotube wire or one twisted carbon nanotube wire.

5. The syringe set of claim 2, wherein in the linear carbon nanotube structure, the carbon nanotubes form a plurality of carbon nanotube wires substantially parallel to each other to form a bundle-like structure or twisted with each other to form a twisted structure.

6. The syringe set of claim 1, wherein the body, the first electrode and the second electrode are flexible.

7. The syringe set of claim 1, wherein the body, the first electrode and the second electrode are transparent.

8. The syringe set of claim 1, further comprising a protective structure, wherein the heating element is sandwiched between the body and the protective structure, and one of the body and the protective structure is directly disposed on the syringe.

9. The syringe set of claim 1, further comprising a first lead terminal and a second lead terminal, wherein the heating element is embedded in the body, and the first lead terminal contacts the first electrode and is exposed out of the body, and the second lead terminal contacts the second electrode and is exposed out of the body.

10. The syringe set of claim 1, wherein the body is rigid and has a substantially tubular jacket sidewall, and the syringe is installed in the tubular jacket sidewall.

11. The syringe set of claim 10, wherein a cross-section view of the body along a direction substantially perpendicular to an axial direction of the tubular jacket sidewall is generally C-shaped with a slot.

12. The syringe set of claim 11, wherein the slot extends along the axial direction of the tubular jacket sidewall.

13. A syringe set comprising:
a syringe; and
a heating device comprising:
  a heating module in thermal engagement with the syringe, the heating module comprising a heating element, a plurality of first electrodes and a plurality of second electrodes, wherein the first electrodes and the second electrodes are alternatively arranged on the heating element, and the heating element is composed of a plurality of carbon nanotubes forming a plurality of electrically conductive paths between adjacent first electrodes and second electrodes; and
  a body supporting the heating module
  wherein the at least one electrically conductive path is adapted to convert a current into a heat and transfer the heat.

14. The syringe set of claim 13, further comprising a first conductive line and a second conductive line, wherein the first electrodes are electrically connected by the first conductive line, and the second electrodes are electrically connected by the second conductive line.

15. The syringe set of claim 14, wherein the first conductive line is electrically connected to a common end of the first electrodes, and the second conductive line is electrically connected to a common end of the second electrodes; the first conductive line and the second conductive line are located at opposite sides of the heating element and spaced apart from the heating element.

16. The syringe set of claim 14, wherein the carbon nanotubes form at least one carbon nanotube film, and the carbon nanotubes of each of the at least one carbon nanotube film are joined end-to-end by van der Waals attractive force therebetween, and the carbon nanotubes of each of the at least one carbon nanotube film are substantially aligned along a direction from the first electrodes to the second electrodes.

17. The syringe set of claim 16, further comprising a first lead terminal and a second lead terminal, wherein the heating element is embedded in the body, and the first lead terminal contacts one of the first electrodes and is exposed out of the body, and the second lead terminal contacts one of the second electrodes and is exposed out of the body.

18. A heating device for an injector comprising:
a body;
a heating module disposed on the body, the heating module comprising a heating element, at least one first electrode and at least one second electrode, wherein the heating element is composed of a plurality of carbon nanotubes forming at least one electrically conductive path between the first electrode and the second electrode and the at least one first electrode and the at least one second electrode electrically connect with the carbon nanotubes; and
a temperature controller having a first end and a second end, wherein the first end is connected with one of the at least one first electrode and the at least one second electrode, and the second end is for connecting with a power supply
wherein the at least one electrically conductive path is adapted to convert a current into a heat and transfer the heat.

19. The heating device of claim 18, wherein the at least one first electrode comprises a plurality of first electrodes, the at least one second electrode comprises a plurality of second electrodes; the first electrodes and the second electrodes are alternatively arranged on the heating element, and the at least one electrically conductive path comprises a plurality of electrically conductive paths between adjacent first electrodes and second electrodes.

20. The heating device of claim 19, further comprising a first lead terminal and a second lead terminal, wherein the heating element is embedded in the body, and the first lead terminal contacts one of the first electrodes and is exposed out of the body, and the second lead terminal contacts one of the second electrodes and is exposed out of the body.

* * * * *